(12) United States Patent
Raupach et al.

(10) Patent No.: US 7,289,595 B2
(45) Date of Patent: Oct. 30, 2007

(54) COMPUTERIZED METHOD AND DEVICE FOR CALCULATING AN ORTHOGONAL X-RAY ATTENUATION OF A SUBJECT USING A MEASURED, X-RAY ATTENUATION REFERENCE

(75) Inventors: Rainer Raupach, Adelsdorf (DE); Andreas Schaller, Erlangen (DE); Christoph Süss, Erlangen (DE); Heiko Wolf, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/418,656

(22) Filed: May 5, 2006

(65) Prior Publication Data

US 2006/0269039 A1    Nov. 30, 2006

(30) Foreign Application Priority Data

May 6, 2005    (DE) ...................... 10 2005 021 020

(51) Int. Cl.
*A61B 6/00* (2006.01)

(52) U.S. Cl. .......................................... 378/4; 378/901
(58) Field of Classification Search ............. 378/4–20, 378/901
See application file for complete search history.

(56) References Cited

U.S. PATENT DOCUMENTS

2005/0058249 A1    3/2005  Wolf et al.

FOREIGN PATENT DOCUMENTS

CN          1389182 A     9/2004

*Primary Examiner*—Courtney Thomas
(74) *Attorney, Agent, or Firm*—Schiff Hardin LLP

(57) ABSTRACT

In method and module for calculation of an orthogonal x-ray attenuation of a subject using a measured reference x-ray attenuation in computed tomography, the reference x-ray attenuation and the orthogonal attenuation are provided as input quantities for an automatic dose control of the computed tomography apparatus. The positioning of the subject with regard to the rotation axis of the computed tomography apparatus is taken into account in the calculation of the orthogonal x-ray attenuation detection of the table height of the subject table.

11 Claims, 2 Drawing Sheets

COMPUTERIZED METHOD AND DEVICE FOR CALCULATING AN ORTHOGONAL X-RAY ATTENUATION OF A SUBJECT USING A MEASURED, X-RAY ATTENUATION REFERENCE

BACKGROUND OF THE INVENTION

1. Field of the Invention

The present invention concerns a method for calculation of an orthogonal x-ray attenuation of a subject using a reference x-ray attenuation measured in the preparation for a diagnostic image acquisition by means of computed tomography, as well as an associated device.

2. Description of the Prior Art

A computed tomography apparatus typically has an x-ray acquisition unit with an x-ray radiator and an x-ray detector arranged opposite each other. The x-ray acquisition unit is mounted such that it can rotate around a rotation axis such that, during rotation, x-ray projection images (radiograms) of a subject arranged approximately centrally to the rotation axis can be acquired from different projection directions. An image (tomogram) of one or more slices of the subject is then generated from these x-ray projection images using numerical back-projection methods. In medical computed tomography, the subject to be examined is a body region of a patient.

To support the subject (in particular the patient) in the beam path of the x-ray acquisition unit, a computed tomography apparatus has subject table that can normally be adjusted in terms of height.

The body region of a patient to be examined by means of a computed tomography apparatus generally causes an x-ray attenuation (subsequently designated as attenuation for short), the strength of which is different for different projection directions. A modern computed tomography (CT) apparatus is frequently equipped with an automatic dose control that adapts the radiation intensity to the magnitude of the attenuation dependent on the projection direction, such that an optimally good image quality is achieved with a low x-ray dose. For parameterization of the automatic dose control, the attenuation is conventionally measured in two reference projection directions orthogonal to one another (in particular anterior-posterior (ap) and lateral), for example using two overview radiograms acquired before the actual diagnostic tomographic data acquisition. The measured values of the ap-attenuation and the lateral attenuation are supplied as reference values to the automatic dose control, which adapts the radiation intensity to these reference values during the diagnostic CT acquisition in a manner dependent on the projection direction. The ap-attenuation and the lateral attenuation are obtained in the form of an axial attenuation profile (i.e. attenuation as a function of the axial location along the body) and supplied to the automatic dose control in order to take into account differences of the attenuation in the longitudinal body direction.

In order to accelerate the workflow associated with a medical CT acquisition, a reference measurement of the attenuation is implemented only in one projection direction (in particular in the ap-projection direction) while the orthogonal attenuation (in particular thus the lateral attenuation perpendicular to this) is estimated using the shadow or contour outline of the subject on the x-ray detector. Such a method typically leads to a correct estimation of the orthogonal attenuation (and therewith to a precise adaptation of the x-ray dose) only when the subject is positioned exactly centrally with regard to the rotation axis in the projection direction. An exact positioning of the subject relative to the rotation axis, however, is not always possible, in particular not simultaneously over the entire axial body length. Given an imprecise positioning of the subject, the orthogonal attenuation is systematically underestimated or overestimated in conventional methods, with the result that x-ray projection images with insufficient signal-to-noise ratio are generated, or that an unnecessarily high x-ray dose is applied during the CT acquisition.

SUMMARY OF THE INVENTION

An object of the present invention is to provide a simple time-saving and simultaneously precise method for calculation of the orthogonal (x-ray) attenuation of a subject using a reference (x-ray) attenuation measured in the preparation for a diagnostic CT acquisition. A further object is to provide a method that enables a correction of the orthogonal attenuation estimated according to a conventional method. A further object of the invention is to provide a device for implementation of such a method.

These objects are achieved in accordance with the present invention by a method to derive an orthogonal (x-ray) attenuation using a reference (x-ray) attenuation (measured along a reference projection direction) of a subject on a subject table, wherein the vertical positioning of the subject with regard to the rotation axis, in particular a deviation of the center of the area of the subject with regard to the rotation axis in the vertical direction, is taken into account in the calculation by detection of the table height.

As a consequence of the detection of the table height and its consideration in the calculation or correction of the orthogonal attenuation, the inventive method enables a precise dose calculation on the basis of only one reference measurement when the subject to be examined is not precisely centrally vertically arranged with regard to the rotation axis. A precise adjustment of the table height is unnecessary. This is particularly of great advantage in lieu of the fact that normally all axial regions of the subject cannot be simultaneously centered by adjustment of the table height.

The method in particular serves for correction of values of the orthogonal attenuation that have been estimated in the framework of convention methods under the assumption that the subject is supported vertically centered relative to the rotation axis. In this application, the estimated orthogonal attenuation (for example supplied in a standard manner by a conventional CT) is used as an input quantity for the inventive method and a corrected orthogonal attenuation is calculated using the table height.

In an embodiment of the invention, the interval distance between the subject table and the rotation axis is used as the table height. The vertical positioning of the subject is appropriately derived from the table height and the subject thickness in the reference projection direction. In this case, the latter is in turn determined from the reference attenuation.

As is also typical in conventional methods, in the medical application the aperior-posterior attenuation is preferably measured as the reference attenuation and the lateral attenuation is calculated as the orthogonal attenuation.

The calculation of the orthogonal attenuation preferably ensues according to $$A_{lat} = A'_{lat}\left(\frac{r_f + h_t - \frac{1}{2} \cdot d_0}{r_f}\right) \quad \text{Equation 1}$$

In equation 1, $A_{lat}$ designates the corrected orthogonal attenuation to be calculated (relative to the distortion due to a non-adjusted table height), $A'_{lat}$ designates the uncorrected orthogonal attenuation $r_f$ designates a focal path radius of the x-ray acquisition unit, i.e. the distance between rotation axis and the focus of the x-ray radiator, $h_t$ designates the distance of the subject table from the rotation axis as a measure for the table height, and $d_0 = \mu^{-1} \log(A_{ap})$ designates the subject thickness in the reference projection direction, wherein $\mu$ is a predetermined average attenuation coefficient of the subject material, and $A_{ap}$ is the measured reference attenuation in the reference projection direction.

If the reference attenuation exists for a number of axial positions of the subject or if the reference attenuation is measured as a function of an axial coordinate (parallel to the rotation axis of the computed tomography apparatus), the orthogonal attenuation is thus also calculated corresponding to these axial positions, or, as a function of the axial coordinate.

The above objects also are inventively achieved by a correction module and a computed tomography apparatus embodying such a correction module (in particular in the framework of an automatic dose control) designed for implementation of the method described above. The correction module can be provided for upgrading existing conventional computed tomography systems.

DESCRIPTION OF THE PREFERRED EMBODIMENTS

Figure 1:
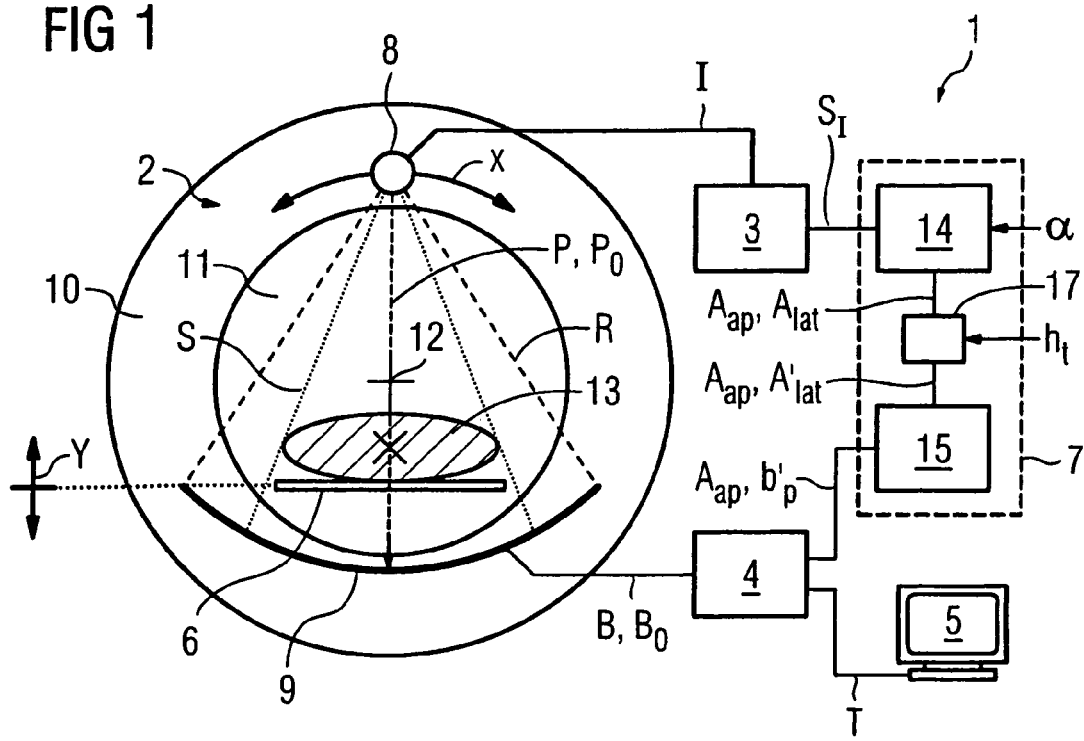
FIG. 1 is a schematic block diagram of a computed tomography apparatus with a correction module for automatic calculation of an orthogonal attenuation of a subject using a measured reference attenuation, in accordance with the present invention.
Figure 2:
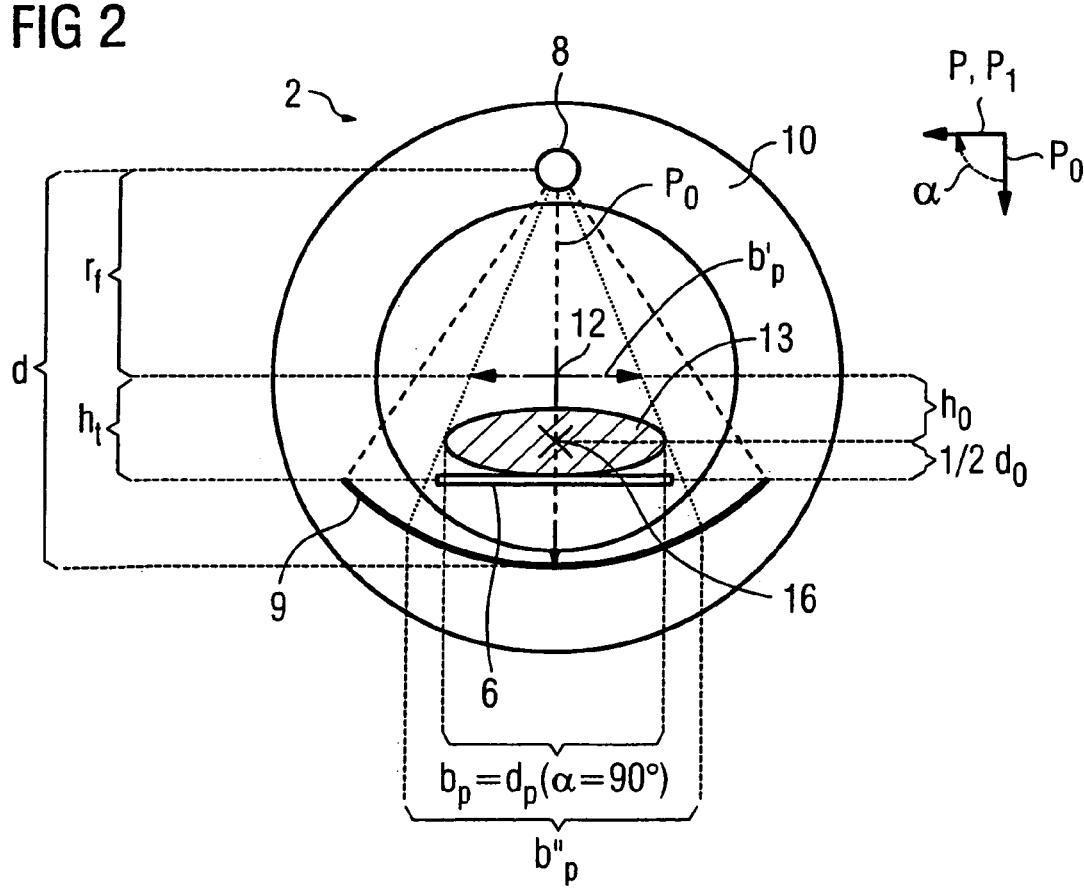
FIG. 2 shows, in section, the x-ray acquisition unit and the subject table of the computed tomography apparatus according to FIG. 1.

The computed tomography apparatus 1 schematically shown in FIG. 1 and 2 has an x-ray acquisition unit 2, a voltage generator 3, an image evaluation unit 4 with downstream display device 5 (in particular a screen), a subject table 6 as well as an automatic dose control 7. The image evaluation unit 4 and the automatic dose control 7 are (in this embodiment) fashioned as software modules and implemented in a computer system (not shown in detail) of the computed tomography apparatus 1.

The x-ray acquisition unit 2 has an x-ray radiator 8 (in the form of an x-ray tube) and an x-ray detector 9. The x-ray radiator 8 and the x-ray detector 9 are mounted on a pivotable mounting 10 (also known as a gantry) that is only outlined in FIG. 1, such that the x-ray radiator 8 and the x-ray detector 9 are fixed in opposition relative to one another with regard to a tunnel-like opening 11 of the pivotable mounting 10, and can be mutually rotated around a rotation axis 12 (also designated as an isocentric axis) in the rotation direction X, by rotation of the pivotable mounting 10. The beam path emanating from the x-ray radiator 8, passing through the rotation axis 12 and impinging centrally on the x-ray detector 9, generally defines a projection direction P dependent on the position of the pivotable frame 10 and the x-ray acquisition unit 2 mounted thereon.

The projection direction P (exemplarily directed perpendicularly downwardly in the representation according to FIGS. 1 and 2) is subsequently designated as a reference projection direction $P_0$. The angle formed between the reference projection direction $P_0$ and an arbitrary second projection direction P is designated as a projection angle $\alpha$ (FIG. 2). The reference projection direction $P_0$ is correspondingly associated with the projection angle $\alpha=0°$.

For the purpose of a tomographical examination, a subject 13 to be examined can be placed on the subject table 6 and inserted into the opening 11 of the pivotable mounting 10 together with the subject table 6. The subject 13 can be the head or back of a patient (schematically represented in FIG. 1 by a hatched oval) or a test subject (for example a water phantom) simulating the human body. For height adjustment of the subject 13, the subject table 6 is height-adjustable in a motorized manner in the adjustment displacement direction Y relative to the pivotable mounting 10 and the x-ray acquisition unit 2 mounted thereon. The subject table 6 can be additionally displaced longitudinally, parallel to the rotation axis 12. With regard to the typical patient borne on the subject table 6 in the dorsal supine position, the reference projection direction $P_0$ corresponds to anterior-posterior (ap) projection.

In operation of the computed tomography apparatus 1, the x-ray radiator 8 generates an x-ray fan beam R at least substantially centered relative to the projection direction P, of which fan beam R a ray section S (indicated dashed in FIG. 1) is transmitted through the subject 13 and is hereby attenuated due to x-ray absorption within the subject 13. The attenuation profile of the x-ray fan beam R so generated is acquired as a (one-dimensional) x-ray projection image B (radiogram) by the x-ray detector 9 arranged behind the subject 13 in the projection direction P, and is forwarded to the image evaluation unit 4. In the course of a CT acquisition, the image evaluation unit 4 calculates a tomogram T of one or more slices of the subject 13 from a number of x-ray projection images B acquired from different projection directions P. The tomogram T can be displayed in the form of a three-dimensional volume representation or as an arbitrary two-dimensional slice representation on the display device 5.

Since the subject 13 normally does not exhibit a rotationally-symmetrical cross-section, the average x-ray attenuation A (subsequently attenuation A for short) caused by the subject 13 is dependent on the projection direction P and therewith on the projection angle $\alpha$.

The (x-ray) attenuation A is generally provided as the radiation intensity measured per detector surface from a given projection angle $\alpha$ given an inserted subject 13, in relation to the radiation intensity measured under different circumstances without the subject 13.

To reduce the x-ray dose, the projection angle-dependent variation of the attenuation A is (at least partially) compensated by adaptation of the radiation intensity generated by the x-ray radiator 8. The radiation intensity is adapted by the magnitude of the current I for the x-ray radiator 8 being adjusted with a corresponding control signal $S_I$ at the x-ray generator 3 that generates this tube current I.

The adjustment of the tube current I ensues with a control module 14 of the automatic dose control 7. The control module 14 determines the current magnitude I according to a predetermined function of the projection angle $\alpha$, with the anterior-posterior attenuation $A_{ap}$ (subsequently designated as ap-attenuation $A_{ap}$) and the lateral attenuation $A_{lat}$ being entered as parameters of this function. The ap-attenuation $A_{ap}$ designates the attenuation A occurring in the reference projection direction $P_0$; the lateral attenuation $A_{lat}$ designates the attenuation A along a second projection direction $P_1$ perpendicular to this (FIG. 2) that runs in the lateral body direction relative to the patient. The ap-attenuation $A_{ap}$ and the lateral attenuation $A_{lat}$ exist as functions of an axial coordinate that is derived from the axial table position. The ap-attenuation $A_{ap}$ and the lateral attenuation $A_{lat}$ thus reproduce the curve of the attenuation over a predetermined axial segment of the subject 13.

The determination of the ap-attenuation $A_{ap}$ as well as of the lateral attenuation $A_{lat}$ ensue in a preparation step (preceding the actual CT diagnostic acquisition of the subject 13) for adaptation of the automatic dose control 7 to the patient geometry. A reference x-ray projection image $B_0$ is initially acquired in the reference projection direction $P_0$, using which reference x-ray projection image $B_0$ the image evaluation unit 4 determines the ap-attenuation $A_{ap}$ as a reference attenuation and supplies this to an adaptation module 15 of the automatic dose control 7.

According to conventional technology, the adaptation module 15 estimates the lateral attenuation $A'_{lat}$ under the assumption that the subject is arranged centered with regard to the rotation axis 12, in that the presumed subject width (i.e. the ray cross-section $b'_P$ at the height of the rotation center 12) is calculated back from the shadow outline of the subject 13 on the x-ray detector 9 (which is indicated in FIG. 2 by the ray cross-section $b''_P$).

The correction module 15 calculates the lateral attenuation $A'_{lat}$ according to $$A'_{lat}=\exp(\mu \cdot b'_P),\qquad\text{Equation 2}$$

wherein the empirically-determined attenuation coefficients $\mu$ (stored as constants) are used.

The more eccentrically that the subject 13 is positioned relative to the rotation axis 12, the more significantly (severely) that the lateral attenuation $A'_{lat}$ estimated in such a manner deviates from the actual lateral attenuation caused by the subject 13. A measure for the vertical positioning of the subject 13 relative to the rotation axis 12 is provided by the vertical distance $h_0$ of the areal center point 16 of the cross-section of the subject 13 from the rotation axis 12.

The more or less adulterated lateral attenuation $A'_{lat}$ is corrected with regard to the actual positioning of the subject 13 in a subsequent correction step that forms the core of the inventive method.

The correction step is effected with a correction module 17 that is interconnected in terms of data flow between the adaptation module 15 and the control module 14.

The correction module 15 calculates the corrected lateral attenuation $A_{lat}$ according to Equation 1 set forth above. The focal path radius $r_f$ entering in equation 1 is established by the dimensioning of the computer tomograph 1 and is predetermined as a constant. The table height $h_t$ provided by the vertical distance between the subject table 6 and the rotation axis 12 is provided to the adaptation module 15 from an apparatus controller (not shown in detail). The subject thickness $d_0$ in the reference projection direction $P_0$ is derived—as described in the preceding—from the ap-attenuation $A_{ap}$ and the attenuation coefficient $\mu$.

The correction module 17 provides the corrected lateral attenuation $A_{lat}$ and the ap-attenuation $A_{ap}$ to the control module 14.

In a manner deviating from the correction method described above, the corrected lateral deviation $A_{lat}$ can also be calculated directly from the ap-attenuation $A_{ap}$, the beam cross-section $b'_P$ and the table height $h_t$, whereby instead of equation 1 the mathematical equivalent equation A4 (stated in the attachment) is used.

To illustrate the method described in the preceding, the focus-detector distance d and the subject width $b_p$ measured perpendicular to the reference projection direction $P_0$ are additionally plotted in FIG. 2 as further geometric parameters. In particular from FIG. 2 it is also apparent that the distance $h_0$ according to $h_o=h_t-\frac{1}{2}\cdot d_0$ is determined by the table height $h_t$.

The mathematical derivation of Equation 1 is set forth in detail below.

Figure 3:
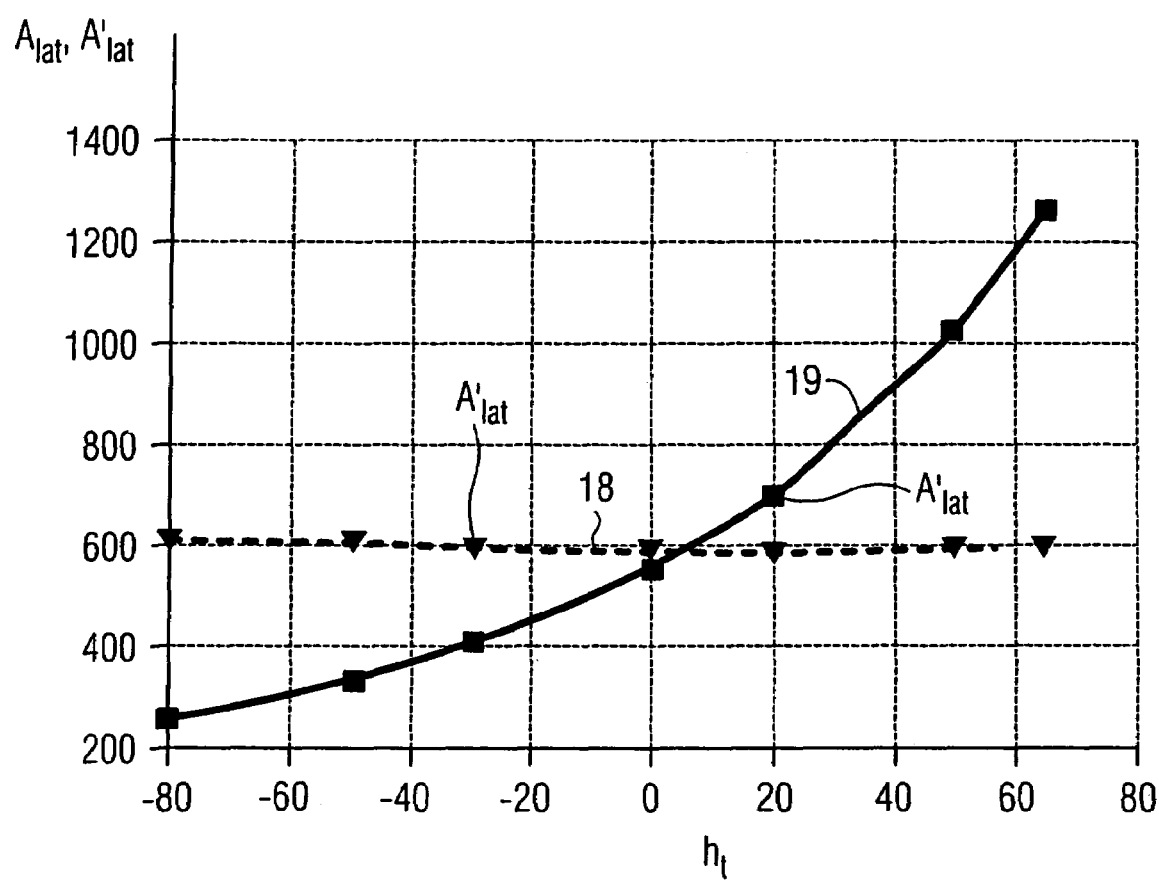
FIG. 3 shows, in a diagram, the lateral attenuation of a test subject (calculated according to the inventive method with table height correction) dependent on the table height, in comparison to the lateral attenuation measured without table height correction.

FIG. 3 shows the result of a test of the method described in the preceding using a diagram of the corrected lateral attenuation $A_{lat}$ (line 18) in comparison to the uncorrected lateral attenuation $A'_{lat}$ (line 19). Both quantities $A_{lat}$ and $A'_{lat}$ are respectively plotted against the table height $h_t$.

A cylindrical water phantom with a diameter of 30 cm is used as a subject 13 for the test. The ap-attenuation $A_{ap}$ and the uncorrected lateral attenuation $A'_{lat}$ was [sic] respectively determined from a reference measurement implemented in reference projection direction $P_0$ for eight various settings of the table height $h_t$ at the water phantom borne on the subject table 6 according to FIG. 1. The corrected later attenuation $A_{lat}$ was calculated from this according to the inventive method using equation 1, i.e. under consideration of the table height $h_t$.

From FIG. 3 it can be recognized that the lateral attenuation $A_{lat}$ (line 18) for various table heights $h_t$ (corresponding to the actual relationships) is constantly determined in good approximation using the inventive method while the uncorrected lateral attenuation $A'_{lat}$ (line 19) incorrectly shows a significant dependence on the table height $h_t$.

Mathematical Derivation of Equation 1:

Notation:

exp ( . . . ) designates the exponential function log ( . . . ) designates the natural logarithm Starting from Equation A1, $$A(\alpha)=\exp(\mu \cdot d_P(\alpha)),\qquad\text{Equation A1}$$

the dependency of the attenuation A on the generalized subject thickness $d_P$ is established for arbitrary projection angles $\alpha$. The subject thickness $d_P$ generally designates the maximal path length that a ray emitted at the projection angle $\alpha$ covers within the subject 13. For the lateral projection direction $P_1$ (i.e. $\alpha=90°$), $d_P(\alpha=90°)=b_P$, compare FIG. 2. For the lateral attenuation, it accordingly follows from equation A1 that $$A_{lat}=A(\alpha=90°)=\exp(\mu \cdot b_P).\qquad\text{Equation A2}$$

From geometric considerations (compare FIG. 2), it follows for $b_P$ that $$b_P = \frac{r_f + h_t - \frac{1}{2}\cdot d_0}{r_f}\cdot b'_P.\qquad\text{Equation A3}$$

From insertion of equation A3 into equation A2 it follows that $$A_{lat} = \exp\left(\mu \cdot \frac{r_f + h_t - \frac{1}{2} \cdot d_0}{r_f} \cdot b'_P\right)$$
$$= \exp(\mu \cdot b'_P)^{\left(\frac{r_f + h_t - \frac{1}{2} \cdot d_0}{r_f}\right)}.$$

Equation A4

Insertion of equation 2 into equation A4 results in equation 1.

The bracket expression $r_f^{-1}(r_f + h_t - \frac{1}{2} \cdot d_o)$ in the exponent of the right side of equation A4 and Equation 1 thus represents a correction with which—in comparison with equation 2—an eccentric positioning of the subject 13 (i.e. of a distance $h_o = h_t - \frac{1}{2} \cdot d_o$ differing from zero) is taken into account.

For the ap-attenuation $A_{ap}$ (i.e. $\alpha=0°$ and $d_o=d_p(\alpha=0°)$), it results from Equation A1 that $$A_{ap} = A(\alpha=90°) = \exp(\mu \cdot d_0).$$

Equation A5

From this it follows for the subject thickness $d_0$ entering into equation A4 that $$d_0 = \frac{1}{\mu} \cdot \log(A_{ap}).$$

Equation A6

The beam cross-section $b'_P$ dealt with in equation 1 can be estimated in a simple approximation according to $$b'_p = \frac{r_f}{d} \cdot b''_p$$

Equation A7 from the shadow outline of the subject 13 on the x-ray detector 9, whereby here the x-ray detector 9 was assumed as planar for simplification. In practice, in particular the curvature of the x-ray detector 9 is additionally taken into account in the determination of $b'_P$.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating an image of a subject by computed tomography with automatic, computerized calculation of an orthogonal x-ray attenuation of a subject supported on a subject table of a computed tomography apparatus using a reference x-ray attenuation measured along a referenced projection direction, said computer tomography apparatus having a rotation axis around which a data acquisition unit is rotatable to obtain computed tomography data, said method comprising the steps of:
   automatically detecting a table height of said subject table in said computed tomography apparatus;
   from said table height, automatically electronically determining a vertical position of the subject with respect to said rotation axis, and automatically electronically calculating said orthogonal x-ray attenuation dependent on said vertical position of the subject with respect to said rotation axis;
   with said data acquisition unit, acquiring said computed tomography data from the subject supported on the subject table at said table height; and
   electronically reconstructing an image of the subject from said computed tomography data using an image reconstruction algorithm employing said orthogonal x-ray attenuation.

2. A method as claimed in claim 1 comprising automatically electronically estimating said orthogonal x-ray attenuation using a shadow outline of the subject and a reference projection in which said reference x-ray attenuation is measured, assuming a central position of said subject relative to said rotation axis, and wherein the step of automatically electronically calculating said orthogonal x-ray attenuation comprises correcting the estimated orthogonal x-ray attenuation dependent on said vertical position of the subject with respect to said rotation axis.

3. A method as claimed in claim 2 comprising automatically electronically determining a distance between the subject table and the rotation axis as said table height.

4. A method as claimed in claim 3 comprising automatically electronically determining said vertical position of the subject from said table height and a subject thickness in said reference projection direction, and determining said subject thickness from said reference x-ray attenuation.

5. A method as claimed in claim 4 comprising automatically electronically calculating said corrected orthogonal attenuation according to the formula;

$$A_{lat} = A'_{lat}{}^{\frac{1}{r_f}(r_f + h_t - \frac{1}{2} \cdot d_0)}$$

wherein
   $A_{lat}$ is the corrected orthogonal attenuation to be calculated,
   $A'_{lat}$ is the orthogonal x-ray attenuation estimated under the assumption of a central positioning of the subject,
   $r_f$ is a focal path radius of the x-ray acquisition unit of the computed tomography apparatus relative to the rotation axis,
   $h_t$ is the distance of the subject table from the rotation axis as a measure of the table height,
   $d_0 = \mu^{-1} \log(A_{ap})$ designates the subject thickness in the reference projection direction $P_0$,
   $\mu$ is a predetermined average attenuation coefficient, and
   $A_{ap}$ is the measured reference attenuation.

6. A method as claimed in claim 1 comprising automatically electronically determining a distance between the subject table and the rotation axis as said table height.

7. A method as claimed in claim 6 comprising automatically electronically determining said vertical position of the subject from said table height and a subject thickness in said reference projection direction, and determining said subject thickness from said reference x-ray attenuation.

8. A module for calculating an orthogonal x-ray attenuation of a subject supported on a subject table of a computed tomography apparatus, using a reference x-ray attenuation measured along a reference projection direction, said computed tomography apparatus having a rotation axis and which a data acquisition unit rotates to obtain computed tomography data, said module automatically electronically detecting a table height of the subject table and automatically electronically determining a vertical position of the subject with respect to the rotation axis from said table height, and said module automatically electronically calculating said orthogonal x-ray attenuation using said vertical position of the subject with respect to the rotation axis.

9. A module as claimed in claim 8 wherein said module is supplied with an estimated orthogonal x-ray attenuation that was estimated using a shadow outline of the subject in a reference projection direction in which said reference x-ray attenuation was measured, under the assumption of a central positioning of the subject relative to the rotation axis, and wherein said module automatically electronically calculates said orthogonal x-ray attenuation by correcting said estimated orthogonal x-ray attenuation dependent on said vertical position of the subject with respect to the rotation axis.

10. A computed tomography apparatus comprising:
   a height-adjustable subject table adapted to receive a subject thereon;
   a computed tomography data acquisition unit that is rotatable around a rotation axis and around the subject on the subject table to obtain computed tomography data from the subject, including a reference x-ray attenuation measured along a referenced projection direction; and
   a module for calculating an orthogonal x-ray attenuation of the subject supported on the subject table, using a reference x-ray attenuation measured along a reference projection direction, said module automatically electronically detecting a table height of the subject table and automatically electronically determining a vertical position of the subject with respect to the rotation axis from said table height, and said module automatically electronically calculating said orthogonal x-ray attenuation using said vertical position of the subject with respect to the rotation axis.

11. A module as claimed in claim 10 wherein said module is supplied with an estimated orthogonal x-ray attenuation that was estimated using a shadow outline of the subject in a reference projection direction in which said reference x-ray attenuation was measured, under the assumption of a central positioning of the subject relative to the rotation axis, and wherein said module automatically electronically calculates said orthogonal x-ray attenuation by correcting said estimated orthogonal x-ray attenuation dependent on said vertical position of the subject with respect to the rotation axis.

* * * * *